(12) United States Patent
Koay et al.

(10) Patent No.: US 10,314,626 B2
(45) Date of Patent: Jun. 11, 2019

(54) WASHER PLATE

(71) Applicant: DePuy Synthes Products, Inc., Raynham, MA (US)

(72) Inventors: Kenny Koay, West Chester, PA (US); Michael Wahl, West Chester, PA (US); Rene Haag, West Chester, PA (US); Robert Limouze, West Chester, PA (US); George Haidukewych, Orlando, FL (US); Bruce H. Ziran, Atlanta, GA (US); Cory A. Collinge, Fort Worth, TX (US); Frank A. Liporace, Fort Lee, NJ (US)

(73) Assignee: DePuy Synthes Procucts, Inc., Raynham, MA (US)

( * ) Notice: Subject to any disclaimer, the term of this patent is extended or adjusted under 35 U.S.C. 154(b) by 628 days.

(21) Appl. No.: 14/599,419

(22) Filed: Jan. 16, 2015

(65) Prior Publication Data
US 2016/0206356 A1  Jul. 21, 2016

(51) Int. Cl.
*A61B 17/72* (2006.01)
*A61B 17/80* (2006.01)

(52) U.S. Cl.
CPC .......... *A61B 17/8052* (2013.01); *A61B 17/72* (2013.01); *A61B 17/7241* (2013.01); *A61B 17/80* (2013.01); *A61B 17/8061* (2013.01)

(58) Field of Classification Search
CPC ............ A61B 17/7233; A61B 17/7241; A61B 17/74–17/748; A61B 17/72–17/88; A61B 17/80–17/809
See application file for complete search history.

(56) References Cited

U.S. PATENT DOCUMENTS

| 3,716,050 A | * | 2/1973 | Johnston ............ | A61B 17/8061 606/286 |
| 3,779,240 A | * | 12/1973 | Kondo ............... | A61B 17/8014 606/282 |
| RE31,628 E | * | 7/1984 | Allgower ........... | A61B 17/8014 606/282 |
| 5,522,902 A | | 6/1996 | Yuan et al. | |

(Continued)

FOREIGN PATENT DOCUMENTS

| EP | 2 590 584 | 4/2014 |
| WO | 2010/117940 | 10/2010 |
| WO | 2012/154496 | 11/2012 |

*Primary Examiner* — Jacqueline T Johanas
(74) *Attorney, Agent, or Firm* — Fay Kaplun & Marcin, LLP

(57) ABSTRACT

A plate for treating a bone includes a plate body extending along a longitudinal axis from a first end to a second end and being sized, shaped and contoured to be positioned along a desired surface of a bone. The plate also includes a slotted opening extending through the plate body and defined by a first portion sized and shaped to permit a head portion of a bone fixation element fixed to the bone to be passed therethrough and a second elongated portion extending along the longitudinal axis from the first portion in communication with the first portion, the second portion sized to prevent the head portion of the bone fixation element from being passed therethrough so that, when the head portion of the bone fixation element is received through the first portion, the plate is slidable relative thereto such that the second portion engages the head portion of the bone fixation element.

13 Claims, 5 Drawing Sheets

(56) References Cited

U.S. PATENT DOCUMENTS

| | | | | |
|---|---|---|---|---|
| 5,951,557 A * | 9/1999 | Luter | A61B 17/80 | 606/286 |
| 8,211,145 B2 * | 7/2012 | Dalton | A61B 17/7059 | 606/246 |
| 8,236,034 B2 * | 8/2012 | Binder | A61B 17/8033 | 606/289 |
| 9,451,996 B2 * | 9/2016 | Jarolem | A61B 17/86 | |
| 2002/0103488 A1 * | 8/2002 | Lower | A61B 17/72 | 606/62 |
| 2002/0173792 A1 * | 11/2002 | Severns | A61B 17/72 | 606/62 |
| 2003/0135212 A1 * | 7/2003 | Y. Chow | A61B 17/72 | 606/64 |
| 2005/0261688 A1 * | 11/2005 | Grady, Jr. | A61B 17/8057 | 606/286 |
| 2006/0095039 A1 * | 5/2006 | Mutchler | A61B 17/72 | 606/64 |
| 2006/0100623 A1 * | 5/2006 | Pennig | A61B 17/72 | 606/64 |
| 2006/0106385 A1 * | 5/2006 | Pennig | A61B 17/72 | 606/64 |
| 2006/0122600 A1 * | 6/2006 | Cole | A61B 17/164 | 606/62 |
| 2007/0016205 A1 * | 1/2007 | Beutter | A61B 17/8057 | 623/17.11 |
| 2007/0219636 A1 * | 9/2007 | Thakkar | A61B 17/1721 | 623/18.11 |
| 2007/0233115 A1 | 10/2007 | Sixto et al. | | |
| 2008/0161854 A1 * | 7/2008 | Bae | A61B 17/7007 | 606/246 |
| 2008/0249572 A1 | 10/2008 | Tandon | | |
| 2008/0262496 A1 | 10/2008 | Schlienger et al. | | |
| 2008/0294164 A1 * | 11/2008 | Frank | A61B 17/744 | 606/64 |
| 2009/0177240 A1 * | 7/2009 | Perez | A61B 17/7233 | 606/86 R |
| 2010/0069906 A1 | 3/2010 | Schwer | | |
| 2010/0249781 A1 * | 9/2010 | Haidukewych | A61B 17/7241 | 606/62 |
| 2010/0256685 A1 | 10/2010 | Plecko et al. | | |
| 2010/0262193 A1 | 10/2010 | Frigg et al. | | |
| 2010/0262194 A1 | 10/2010 | Wagner et al. | | |
| 2010/0298829 A1 | 11/2010 | Schaller et al. | | |
| 2011/0190769 A1 * | 8/2011 | Haininger | A61B 17/72 | 606/64 |
| 2011/0202093 A1 * | 8/2011 | Grady, Jr. | A61B 17/746 | 606/290 |
| 2012/0265255 A1 * | 10/2012 | Hilse | A61B 17/8014 | 606/290 |
| 2013/0030435 A1 | 1/2013 | Perez | | |
| 2013/0172943 A1 * | 7/2013 | Austin | A61B 17/74 | 606/284 |
| 2013/0204250 A1 * | 8/2013 | McDevitt | A61B 17/0401 | 606/64 |
| 2013/0238034 A1 | 9/2013 | Graham | | |
| 2013/0345707 A1 * | 12/2013 | Winslow | A61B 17/8061 | 606/71 |
| 2014/0309703 A1 * | 10/2014 | Ducharme | A61B 17/8057 | 606/289 |
| 2014/0316473 A1 * | 10/2014 | Pfeiffer | A61B 17/8057 | 606/291 |
| 2014/0378973 A1 | 12/2014 | Mueckter | | |
| 2015/0105779 A1 * | 4/2015 | Smith | A61B 17/1725 | 606/71 |
| 2015/0201981 A1 * | 7/2015 | Hilse | A61B 17/8014 | 606/282 |
| 2015/0257802 A1 * | 9/2015 | Wolf | A61B 17/8061 | 606/291 |

\* cited by examiner

1

WASHER PLATE

BACKGROUND

As the indications for joint replacements have expanded, periprosthetic fractures are becoming more common. In some cases, placement of the prosthetic may predispose the bone to later fracture and/or the prosthetic may interfere with the healing of other portions of the bone. Osteopenic patients may be particularly susceptible to periprosthetic fractures. Periprosthetic fractures, however, are often difficult to treat because of the placement of the prior implanted prosthetics and/or poor bone quality.

SUMMARY OF THE INVENTION

The present invention is directed to a plate for treating a bone, comprising a plate body extending along a longitudinal axis from a first end to a second end and being sized, shaped and contoured to be positioned along a desired surface of a bone and a slotted opening extending through the plate body from a first surface which, when the plate is positioned along the desired surface of the bone faces away from the bone, to a second surface which, when the plate is positioned along the desired surface faces toward the bone, the slotted opening defined by a first portion sized and shaped to permit a head portion of a bone fixation element fixed to the bone to be passed therethrough and a second elongated portion extending along the longitudinal axis from the first portion in communication with the first portion, the second portion sized to prevent the head portion of the bone fixation element from being passed therethrough so that, when the head portion of the bone fixation element is received through the first portion, the plate is slidable relative thereto such that the second portion engages the head portion of the bone fixation element.

BRIEF DESCRIPTION

DETAILED DESCRIPTION

Figure 1:
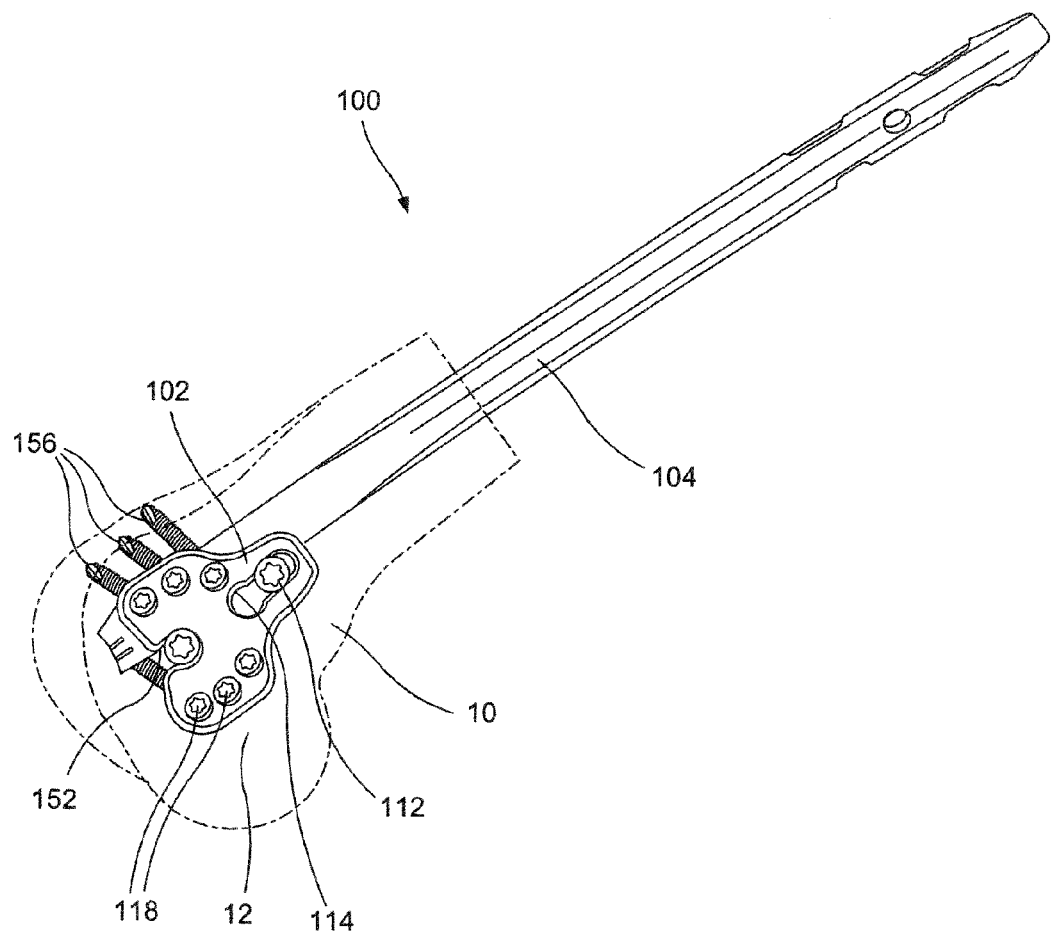
FIG. 1 shows a perspective view of a system according to an exemplary embodiment of the present invention.
Figure 2:
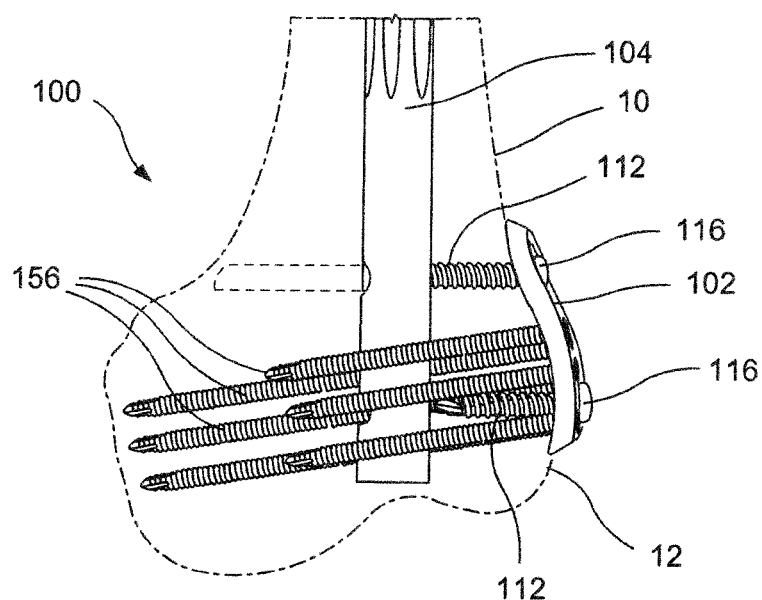
FIG. 2 shows an anterior-posterior view of the system of FIG. 1.
Figure 3:
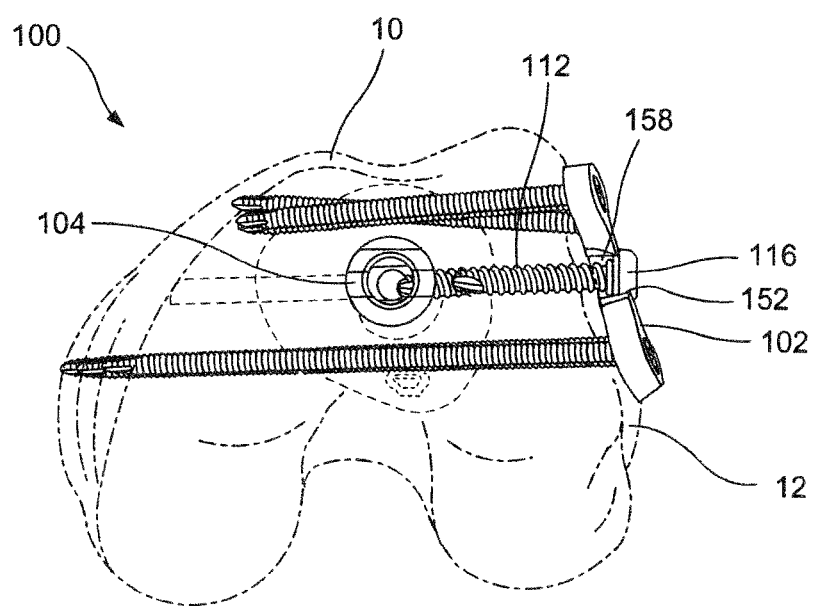
FIG. 3 shows an inferior-superior view of the system of FIG. 1, viewed from a distal end of a bone.

The present invention may be further understood with referenced to the following description and the appended drawings, wherein like elements are referred to with the same reference numerals. The present invention is directed to a system for treating a bone and, in particular, to a system for treating bone fractures. Exemplary embodiments of the present invention describe a system comprising a washer plate, which may be implanted along a surface of a bone (e.g., distal femur) to provide additional fixation and/or support to the bone without interfering with previously implanted fixation elements such as, for example, an intramedullary nail and/or a knee prosthetic implanted during an arthroplasty procedure. Although exemplary embodiments of the present invention specifically show and describe a washer plate implanted along a distal femur, it will be understood by those of skill in the art that the washer plate may be used to treat any number of fractures/weaknesses in any of a variety of bones such as, for example, the tibia or the humerus. It will also be understood by those of skill in the art that although the exemplary embodiments are described with respect to periprosthetic fractures resulting subsequent to, for example, an arthroplasty procedure, the system of the present invention is not limited to use with prior implanted prosthetics.

As shown in FIGS. 1-7, a system 100 for treating a bone according to an exemplary embodiment of the present invention comprises a washer plate 102 configured to be fixed to a surface of a bone subsequent to placement of an intramedullary nail 104 to provide additional fixation and/or support to the bone without interfering with the placement of the intramedullary nail 104. The washer plate 102 may include a first slotted opening 114 and a second hole 152 extending therethrough, each of the first slotted opening 114 and the second hole 152 configured to receive and engage a head portion 116 of a locking screw 112 that has been previously inserted into a locking hole 110 of the intramedullary nail 104 to fix the intramedullary nail 104 relative to the bone. The slotted opening 114 engages the head portion 116 of the locking screw 112 in a slot and keyhole fashion to allow the washer plate 102 to be positioned along and/or removed from a bone without disturbing the prior-implanted intramedullary nail 104. The second hole 152 is laterally open to an exterior of the washer plate 102 so that sliding the washer plate 102 along the bone to engage a first locking screw 112 with an elongated portion 148 of the slotted opening 114 causes the second opening 152 to be slidably engaged with a second locking screw 112 via a lateral opening 158 thereof. Thus, a position and orientation of the washer plate 102 along the bone may be determined without the use of any additional instruments. The washer plate 102 also includes a plurality of holes 118 configured to receive fixation elements for fixing the washer plate 102 to the bone once the washer plate 102 has been positioned therealong.

Figure 4:
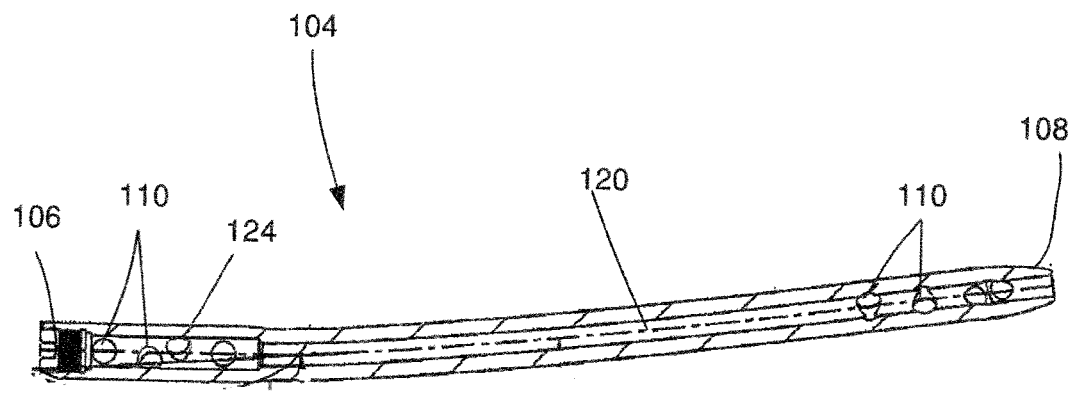
FIG. 4 shows a longitudinal cross-sectional view of an intramedullary nail according to the system of FIG. 1.
Figure 5:
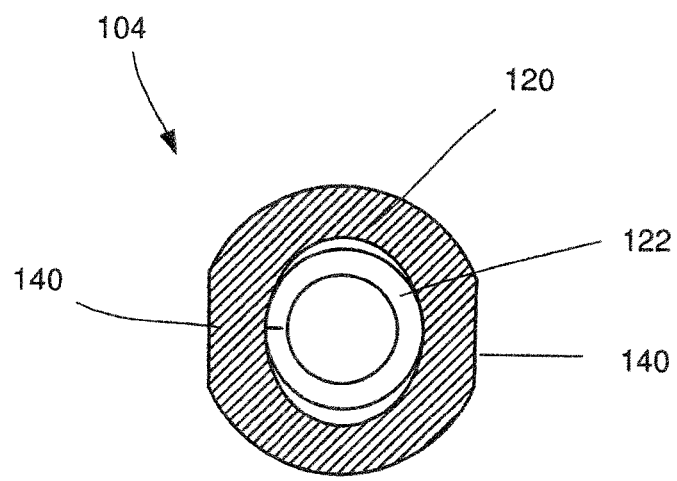
FIG. 5 shows a lateral cross-sectional view of the intramedullary nail of FIG. 4.

As shown in FIGS. 4 and 5, the intramedullary nail 104 extends longitudinally from a first end 106 to a second end 108 and includes a channel 120 extending longitudinally therethrough. The intramedullary nail 104 also includes a plurality of locking holes 110 extending laterally therethrough. In particular, locking holes 110 may extend along portions of the intramedullary nail 104 proximate the first and second ends 106, 108. The intramedullary nail 104 may further include an insert 122 received within the channel 120 along at least a head portion 124 of the intramedullary nail 104 through which the locking holes 110 proximate the first end 106 extend. The insert 122 may be formed of a polymer material such as, for example, polyethylene, so that, when a locking screw 112 is inserted through one of the locking holes 110 along the head portion 124, the locking screw 112 forms a passage through the insert 122. The insert 122 stabilizes the locking screw 112 within the locking hole 110 to prevent any relative movement therebetween. In another embodiment, the intramedullary nail 104 does not include the insert 122 within the channel 120 thereof. Rather, the locking screw 112 may be an angularly stable locking screw which expands upon insertion into the locking hole 110 to fix the locking screw 112 therein in an angularly stable fashion, preventing relative movement therebetween. Angular stability between the intramedullary nail 104 and the locking screw 112 also facilitates a locking of the washer plate 102 to the bone, as the locking screws 112 may be subsequently backed out to engage the washer plate 102.

In an exemplary embodiment in which the system 100 is used to fix fractures along a distal femur 10, the second end 108 of the intramedullary nail 104 may be inserted through, for example, a distal end of the femur 10 into an intramedullary canal thereof such that, when the intramedullary nail 104 is in a desired position within the femur 10, the head portion 124 is positioned at the distal end of the femur 10. Once inserted in the femur 10, as would be understood by those skilled in the art, the intramedullary nail 104 is fixed therein via one or more locking screws 112. It will be understood by those of skill in the art that the intramedullary nail 104 may have been previously implanted in the femur 10 to fix a fracture extending along a portion thereof. Alternatively, the intramedullary nail 104 may be inserted into the femur 10 for the purpose of fixing the washer plate 102 thereto.

The intramedullary nail 104 may also include planar portions 140 extending along a portion of a length thereof. In particular, the planar portions 140 may extend along the portion of the length of the intramedullary nail 104 which, when the intramedullary nail 104 is inserted into the bone, extends along the shaft portion of the bone. The intramedullary nail 140 may include first and second planar portions 140 diametrically opposing one another. As would be understood by those skilled in the art, the planar portions 140 permit the intramedullary nail 104 to have a larger diameter while still facilitating insertion thereof into the medullary canal of the bone.

Figure 6:
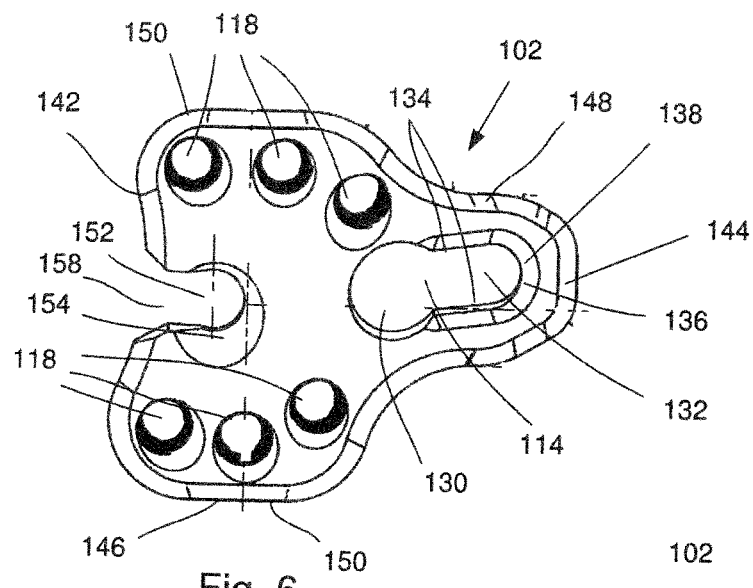
FIG. 6 shows a top plan view of a washer plate according to the system of FIG. 1.
Figure 7:
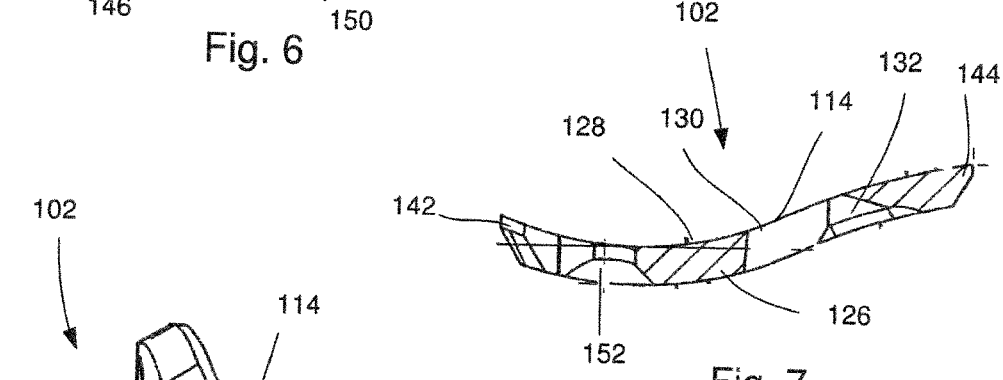
FIG. 7 shows a cross-sectional view of the washer plate of FIG. 6, along line A-A.
Figure 8:
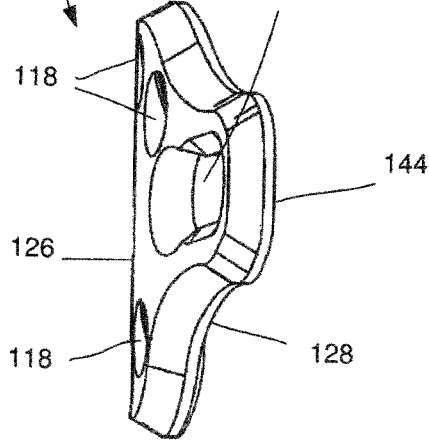
FIG. 8 shows a side view of the washer plate of FIG. 6.
Figure 9:
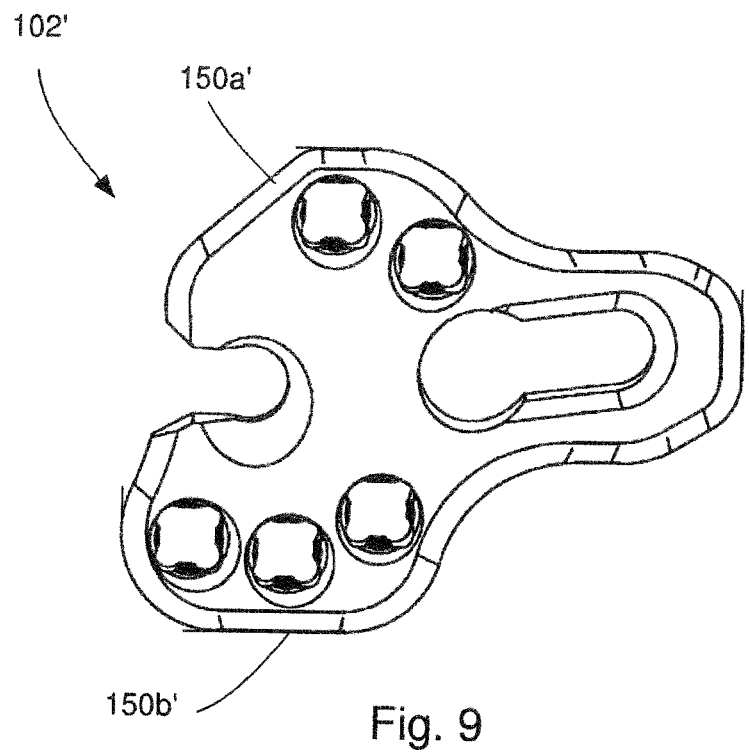
FIG. 9 shows a washer plate according to another exemplary embodiment of the present invention.

As shown in FIGS. 6-8, the washer plate 102 may be sized, shaped and contoured to be positioned along, for example, a lateral surface 12 of the distal femur 10. The washer plate 102 extends from a first end 142 to a second end 144 along a longitudinal axis such that a width (i.e., a distance between longitudinal edges 150 of the washer plate 102) of a first portion 146 of the washer plate 102 may be larger than a width of a second portion 148 of the washer plate 102. The longitudinal edges 150 extending along the first portion 146 may be substantially parallel to one another. In another exemplary embodiment, shown in FIG. 9, a portion of a first longitudinal edge 150a' of a washer plate 102' may be angled with respect to a second longitudinal edge 150b'. In particular, the longitudinal edge 150a' may taper toward a first end 142' of the plate 102' so that, when the washer plate 102' is positioned along, for example, the lateral surface 12 of the distal femur 10, the washer plate 102' does not interfere with any knee prosthetics implanted on the distal femur 10.

The washer plate 102 includes the slotted opening 114 extending therethrough from a first surface 126 which, when the washer plate 102 is positioned along the lateral surface 12, faces away from the bone, to a second surface 128 which, when the washer plate 102 is positioned along the lateral surface 12, faces the bone. The slotted opening 114 according to this embodiment extends along the longitudinal axis of the washer plate 102 through the second portion 148 of the plate 102 and may be defined by a first substantially circular portion 130 and a second elongated portion 132 extending longitudinally therefrom in communication with the first circular portion 130. In an exemplary embodiment, the second elongated portion 132 extends proximally from the circular portion 130, when the washer plate 102 is positioned along the distal femur 10. The first portion 130 is sized and shaped to receive the head portion 116 of the locking screw 112 therein while a width of the second elongated portion 132 (e.g., a distance between longitudinal sides 134 of the elongated portion 132) is smaller than a diameter of the head portion 116 to prevent the head portion 116 from being passed therethrough. A periphery 136 of the second portion 132 along the first surface 126 includes a concave surface 138 configured to seat the head portion 116 of the locking screw 112. In use, the washer plate 102 is positioned along the surface of the bone with the head portion 116 of the screw 112 received in the first portion 130. Once the head portion 116 is received in the first portion 130, the washer plate 102 is slid longitudinally (e.g., distally) along the bone so that the head portion 116 engages the second portion 132 and is seated within the concave surface 138.

The washer plate 102 may also comprise the second hole 152 extending therethrough from the first surface 126 to the second surface 128. The second hole 152 extends through the first portion 146 of the plate 102 proximate the first end 142 and is laterally open to an exterior of the plate 102 via a lateral opening 158 at the first end 142. The second hole 152 is sized and shaped to receive a bone fixation element therein and includes a concave surface 154 extending about a periphery of the second hole 152 along the first surface 126 for seating a head portion of a bone fixation element therein. The lateral opening 158 is sized to permit a shaft portion of a locking screw 112 to be inserted laterally therein. The second hole 152 according to this embodiment extends through the washer plate 102 along the longitudinal axis so that the slotted opening 114 and the second hole 152 are substantially aligned therealong. Thus, after the head portion 116 of a first locking screw 112 is received within the circular portion 130 of the slotted opening 114, the washer plate 102 may be slid longitudinally (e.g., toward the distal end of the bone) so that the first locking screw 112 engages the second elongated portion 132 while a head portion 16 of a second locking screw 112 engages the concave surface 154 of the second hole 152 via the lateral opening 158.

The washer plate 102 further comprises a plurality of holes 118 each of which is sized and shaped to receive a bone fixation element 156 therein to fix the washer plate 102 to the bone. Each of the holes 118 extends through the washer plate 102 from the first surface 126 to the second surface 128 with the holes 118 positioned on either side of the longitudinal axis of the plate 102. In one exemplary embodiment, the washer plate 102 includes six holes 118, three holes 118 on a first side of the longitudinal axis and three holes 118 on a second side of the longitudinal axis opposite the first side. It will be understood by those of skill in the art that the washer plate 102 may include any number of holes 118 in any number of configurations for fixing the washer plate 102 to bone so long as portions of the washer plate 102 on opposing sides of the longitudinal axis each include at least one hole 118. As would be understood by those skilled in the art, any or all of the holes 118 may be a variable angle hole configured to receive a corresponding one of the bone fixation elements 156 therein at a user-selected angle relative to a central axis of the hole 118. Thus, upon positioning of the washer plate 102 over the bone, the user (e.g., surgeon) may insert bone fixation elements 156 through the holes 118 and into the bone at angles relative to axes of the holes 118 selected by the user to prevent interference with the intramedullary nail 104. As would be further understood by those skilled in the art, any of the holes 118 that are not variable angle holes may be locking holes, each of which receives a bone fixation element 156 along a predetermined axis to prevent the bone fixation element 156 inserted in each hole is prevented from interfering with the intramedullary nail 104.

Figure 10:
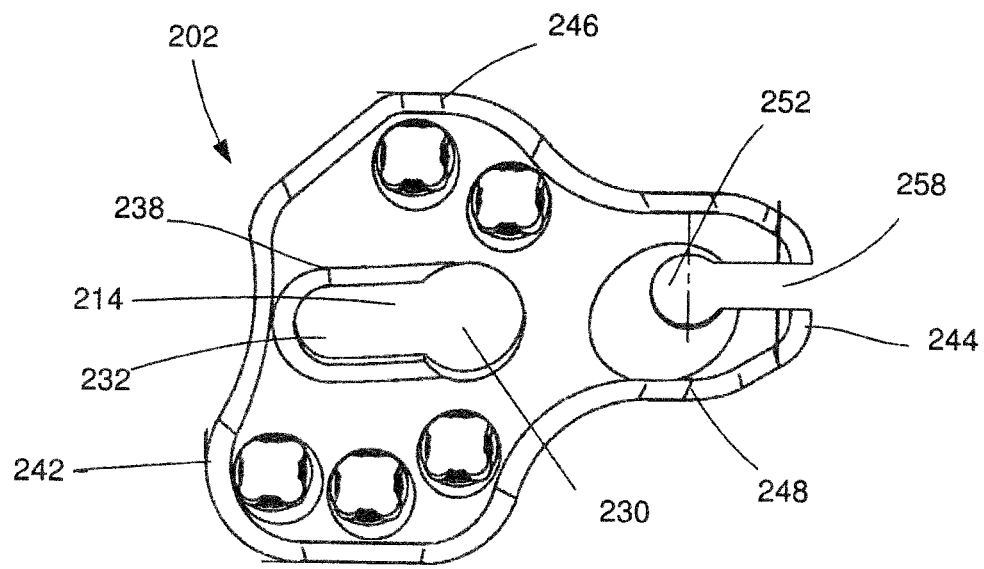
FIG. 10 shows a washer plate according an alternate embodiment of the present invention.

As shown in FIG. 10, a washer plate 202 according to an another embodiment of the present invention may be substantially similar to the washer plate 102. A slotted opening 214 of the washer plate 202, however, extends through a first portion 246 of the plate 202 while a second hole 252 extends through a second portion 248 of the plate 202. The slotted opening 214 includes a first substantially circular portion 230 and a second elongated portion 232 extending longitudinally therefrom. The second elongated portion 232, however, extends distally from the first portion 230 toward a first end 242 of the washer plate 202, when the washer plate 202 is in a desired position along a bone. In addition, the second hole 252 may be substantially similar to the second hole 152 including a concave surface 254 extending thereabout, but is laterally open to an exterior of the washer plate 202 via a lateral opening 258 at a second end 244 of the washer plate 202. Thus, upon receiving a head portion of a screw in the first portion 230, the washer plate 202 is slid toward a proximal end of the bone until the head portion of a first screw engages the second elongated portion 230 of the slotted opening 214 to be seated within a concave surface 238 thereof and a second screw is received within the second hole 252 via the lateral opening 258 so that a head portion thereof is seated in the concave surface 254.

According to another embodiment, any of the slotted openings 114, 214 and the second holes 152, 252 of the washer plates 102, 202 described above may be replaced with locking and/or variable angle holes. In this particular embodiment, the washer plate may be attached to the same aiming arm as the intramedullary nail 104 so that the locking screws may be inserted into both the washer plate and the intramedullary nail 104 at the same time.

Although the exemplary embodiments show and describe the washer plates 102, 202 as being sized and shaped to be positioned along the lateral surface of the distal femur, in another embodiment, a length of the second portion 148, 248 may be selected to extend along at least a portion of the shaft portion of the bone toward a proximal end thereof. In addition, the washer plates 102, 202 may be similarly configured to be positioned along a medial surface of the bone rather than the lateral surface. In an embodiment in which the second portion 148, 248 is elongated to extend along the shaft portion of the bone, the second portion 148, 248 may include a plurality of variable angle holes, locking holes and/or an elongated slot. The variable angle holes may be configured to receive bone fixation elements therein at a user selected angle within a permitted range of angulations relative to central axes of the variable angle holes. The locking holes may extend along axes that are angled so that when bone fixation elements are inserted therein, the bone fixation elements do not interfere with an intramedullary nail inserted into the bone. An elongated slot may be configured to receive a nail locking bolt therein. In another embodiment, the elongated second portion 148 may include a plurality of combination holes including a first portion and a second portion. The first portion may be configured to receive a first bone fixation element therein at a user selected angle within a permitted range of angulations relative to central axes thereof. The second portion may include a concave surface extending thereabout for receiving a second bone fixation element therein so that a head of the second bone fixation element may be seated in the concave surface thereof. It will be understood by those of skill in the art that the second portion 148, 248 may include any of a variety of openings configured to receive a variety of bone fixation elements (e.g., variable angle, locking, cortex screws) therein to lock the washer plate 102, 202 to the shaft portion of the bone.

According to an exemplary surgical technique using the system 100, the intramedullary nail 104 may be inserted through the medullary canal of the distal femur 10 until the head portion 124 of the intramedullary nail is within the distal end of the femur 10. Once the intramedullary nail 104 is in a desired position within the femur 10, locking screws 112 may be inserted through the locking holes 110 of the intramedullary nail 104 to fix the nail 104 relative to the bone. As discussed above, the intramedullary nail 104 may have been inserted into the femur 10 during a prior procedure, in which case, the locking screws 112 would have been inserted into the femur 10 until the head portions 116 thereof abut the bone. When it is desired to mount the washer plate 102 along the femur 10, two of the locking screws 112 extending through locking holes 110 along the head portion 124 of the intramedullary nail 104 are rotated in an unscrewing direction to withdraw the bone screws slightly out of the bone so that the head portion 116 is separated from the lateral surface 12 of the femur 10 by a small distance. For cases in which the intramedullary nail 104 is being inserted into the femur 10 to facilitate fixation of the washer plate 102, the locking screws 112 should be inserted through a locking hole 110 extending through the head portion 124 until the head portions 116 of the locking screws 112 is separated from the bone by only a small distance.

The washer plate 102 may then be positioned along the lateral surface 12 of the distal femur 10 so that the first end 142 of the plate 102 is positioned toward the distal end of the femur 10 while the second end of the plate 102 is positioned toward the proximal end of the femur 10. The washer plate 102 is positioned along the lateral surface 12 such that the head portion 116 of the screw 112, which is distanced from the bone, is received within the first portion 130 of the slotted opening 114. As discussed above, the head portion 116 of the first locking screw 112 is separated from the lateral surface 12 by a small distance. This distance should be sufficient to permit the head portion 116 to be passed through the first portion 130 so that the head portion 116 extends beyond the first surface 126 of the washer plate 102. Thus, when the washer plate 102 is slid distally relative to the femur 10, the head portion 116 engages the longitudinal edges 134 of the second elongate portion 132 and is seated within the concave surface 138 thereof. Simultaneously, the head portion 116 of the second locking screw 112 is received within the second hole 152 via the lateral opening 158 so that the head portion 116 of the second locking screw 112 is seated within the concave surface 154. Thus, the washer plate 102 may be positioned along the femur 10 without the use of any additional positioning and/or aiming instruments.

Once the washer plate 102 is in the desired position along the femur 10, bone fixation elements 156 may be inserted into the plurality of holes 118 to fix the washer plate 102 to the bone. Each of the bone fixation elements 156 is inserted into a corresponding one of the plurality of holes 118 at an angle selected to prevent interference of the bone fixation elements 156 with the intramedullary nail 104. Since the washer plate 102 includes at least one hole 118 on each of the opposing sides of the longitudinal axis of the plate 102, at least one bone fixation element 156 should be inserted through both an anterior and posterior side of the femur 10 on each of the opposing sides of the intramedullary nail 104.

It will be apparent to those skilled in the art that variations can be made in the structure and methodology of the present disclosure, without departing from the scope of the invention. Thus, it is intended that the present disclosure cover the modifications and variations of this invention provided that they come within the scope of the appended claims and their equivalents.

What is claimed is:

1. A plate for treating a bone, comprising:
   a plate body extending along a longitudinal axis from a first end to a second end and being sized, shaped and contoured to be positioned along a desired surface of a bone;
   a slotted opening extending through the plate body from a first surface which, when the plate is positioned along the desired surface of the bone faces away from the bone, to a second surface which, when the plate is positioned along the desired surface faces toward the bone, the slotted opening defined by a first portion sized and shaped to permit a first head portion of a first bone fixation element fixed to the bone to be passed therethrough and a second elongated portion extending along the longitudinal axis from the first portion in communication with the first portion, the second portion sized to prevent the first head portion of the first bone fixation element from being passed therethrough so that, when the first head portion of the first bone fixation element is received through the first portion, the plate is slidable relative thereto such that the second portion engages the first head portion of the first bone fixation element; and
   a second hole extending through the plate body from the first surface to the second surface and being open to an exterior of the plate body via a lateral opening, the second hole sized and shaped to slidably engage a second head portion of a second bone fixation element via the lateral opening.

2. The plate of claim 1, wherein the second elongated portion extends from the first portion toward the second end of the plate body and the lateral opening is at the first end of the plate body.

3. The plate of claim 1, wherein the second elongated portion extends from the first portion toward the first end of the plate body and the lateral opening is at the second end of the plate body.

4. The plate of claim 1, further comprising a plurality of locking holes extending through the plate body from the first surface to the second surface, each of the plurality of locking holes configured to receive a locking bone fixation therein at a user-selected angle relative to a central axis thereof.

5. The plate of claim 4, wherein a first one of the plurality of locking holes extends through the plate body on a first side of the longitudinal axis and a second one of the plurality of locking holes extends through the plate body on a second side of the longitudinal axis opposite the first side.

6. The plate of claim 1, wherein a longitudinal edge of the plate body is tapered toward the first end.

7. The plate of claim 1, wherein a distance between longitudinal edges of a first portion of the plate body is larger than a distance between longitudinal edges of a second portion of the plate body.

8. A system for treating a bone, comprising:
   an intramedullary nail extending longitudinally from a first end to a second end and including a nail locking hole extending transversely therethrough;
   a plate sized, shaped and contoured to be positioned along a surface of a bone through which the intramedullary nail is inserted, the plate including: (1) a slotted opening extending therethrough from a first surface which, when the plate is positioned along the desired surface faces toward the bone, the slotted opening defined by a first portion and a second portion open in communication with one another, the first portion sized and shaped to permit a first head portion of a first bone fixation element inserted into the bone and through the nail locking hole to be passed therethrough, the second portion extending longitudinally from the first portion and being sized to prevent the first head portion of the first bone fixation element from being passed therethrough so that, when the first head portion of the first bone fixation element is received through the first portion, the plate is slidable relative thereto such that the second portion engages the first head portion of the first bone fixation element; and (2) a second hole extending through the plate body from the first surface to the second surface and being open to an exterior of the plate body via a lateral opening, the second hole sized and shaped to slidably engage a second head portion of a second bone fixation element via the lateral opening.

9. The system of claim 8, wherein the second hole includes a concave surface extending about a periphery thereof.

10. The system of claim 8, further comprising an insert received within a channel extending longitudinally through the intramedullary nail, the insert extending along a portion of the intramedullary nail through which the nail locking hole extends to stabilize a locking fixation element received within the nail locking hole.

11. The system of claim 8, wherein the second portion of the slotted opening includes a concave surface extending along the first surface about a periphery thereof.

12. The system of claim 8, further comprising a plurality of plate locking holes extending through the plate body from the first surface to the second surface, each of the plurality of plate locking holes configured to receive a locking bone fixation element therein at a user-selected angle relative to a central axis thereof.

13. The system of claim 12, wherein a first one of the plurality of plate locking holes extends through the plate body on a first side of the longitudinal axis and a second one of the plurality of plate locking holes extends through the plate body on a second side of the longitudinal axis opposite the first side.

* * * * *